(12) United States Patent
Bolle et al.

(10) Patent No.: US 7,508,960 B1
(45) Date of Patent: Mar. 24, 2009

(54) PROJECTION OF LIGHT PATTERNS FOR LIVENESS VERIFICATION OF BIOMETRICS

(75) Inventors: Rudolf M. Bolle, Bedford Hills, NY (US); Jonathan H. Connell, II, Cortlandt Manor, NY (US); Nalini K. Ratha, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/115,584

(22) Filed: May 6, 2008

(51) Int. Cl.
*G06K 9/00* (2006.01)
*G06K 9/64* (2006.01)
*G05B 19/00* (2006.01)
*A61B 3/10* (2006.01)
*G06K 9/68* (2006.01)

(52) U.S. Cl. ............... 382/117; 382/115; 382/217; 340/5.82; 351/211

(58) Field of Classification Search ......... 382/115–118, 382/190, 217, 218; 340/5.52–5.53, 5.82–5.84; 356/51, 71, 300; 351/211; 902/3, 5, 6
See application file for complete search history.

(56) References Cited

U.S. PATENT DOCUMENTS

2006/0072122 A1* 4/2006 Hu et al. ............... 356/603
2007/0047774 A1* 3/2007 Yukhin et al. ............ 382/118
2007/0110285 A1 5/2007 Hanna et al.

* cited by examiner

*Primary Examiner*—Yon Couso
(74) *Attorney, Agent, or Firm*—Cantor Colburn LLP; Joseph Jones

(57) ABSTRACT

The biometric system disclosed herein comprises device for providing a pattern; the device having a source of light and a source for providing a pattern. The source of light is operative to illuminate an object with light. An imaging device is disposed at a different location from the source of light to capture an image from the object. The system further comprises a pattern comparison device; the pattern comparison device being operative to compare details of the pattern disposed upon the object and details of a reference pattern; the pattern comparison device rejecting the object if the pattern disposed upon the object does not match the reference pattern.

6 Claims, 3 Drawing Sheets flat iris curved contact

PROJECTION OF LIGHT PATTERNS FOR LIVENESS VERIFICATION OF BIOMETRICS

BACKGROUND

This disclosure relates the projection of patterns for liveness verification of biometrics.

Biometrics includes the study of methods for uniquely recognizing humans based upon one or more intrinsic physical or behavioral traits. Many biometric identification methods already exist for face recognition and for iris prints. Some systems even have liveness checks such as watching for eyeblinks in a face or for the pulsation of the pupil in an iris image. However, these methods do not try to recover the 3-dimensional geometry of the object that is being imaged.

The 3-dimensional geometry of an object, such as, for example, a human face may however be determined in a number of different ways. One method of doing so involves taking images of a human face with a pair of offset cameras and using the images to perform a stereo depth computation. This method has the advantage of being passive, i.e., no energy is emitted. However, it is expensive because of the use of two cameras. It is also expensive computationally.

It is therefore desirable to have an inexpensive method by which the 3-dimensional shape of a characteristic portion of a face or any other feature of the human body can be imaged and determined.

SUMMARY

Disclosed herein is a biometric system comprising a device for providing a pattern; the device comprising a source of light; the source of light being of an intensity that is effective to project a pattern onto a diffusely reflecting object; and a source for providing the pattern; the source for providing the pattern being disposed between the source of light and the diffusely reflecting object upon which an image of the pattern is disposed; the source for providing the pattern being illuminated by the source of light; the pattern being disposed upon the object; an imaging device; the imaging device being disposed at a different location from the source of light; the imaging device being operative to obtain an image from light that is diffusely reflected from the object; a pattern comparison device; the pattern comparison device being operative to compare details of the pattern disposed upon the object and details of a reference pattern; and a biometric comparison device; the biometric comparison device being effective to compare an image of the object to one or more known images to make a biometric identification; the pattern comparison device rejecting the identification, if the pattern disposed upon the object does not match the reference pattern.

DETAILED DESCRIPTION

Disclosed herein is a system and a method for determining the shape of an object, such as for example, a human face. The method comprises disposing an image of a pattern or an image of the edge of an opaque screen, on the object. The shape of the image on the object can be analyzed to determine whether the object is a true object or a replica that has a different shape to it.

The method disclosed herein is advantageous in that it can be used to determine whether the object being observed has the correct physical shape. The check eliminates some possible means of gaining fraudulent entry to a secure system or area. For instance, a human face is curved and has a protruding nose, whereas a 8 inch×10 inch photograph of the same face does not have this physical structure. Similarly, a true iris (part of the human eye) is essentially flat, whereas a printed contact lens has a spherical surface. These differences can be used for security enhancement. In one embodiment, the curvature of the image that is disposed on the object is used to determine whether the object is that of a true human being or that of an image of the human being (e.g., a 2-dimensional imposter).

Figure 1:
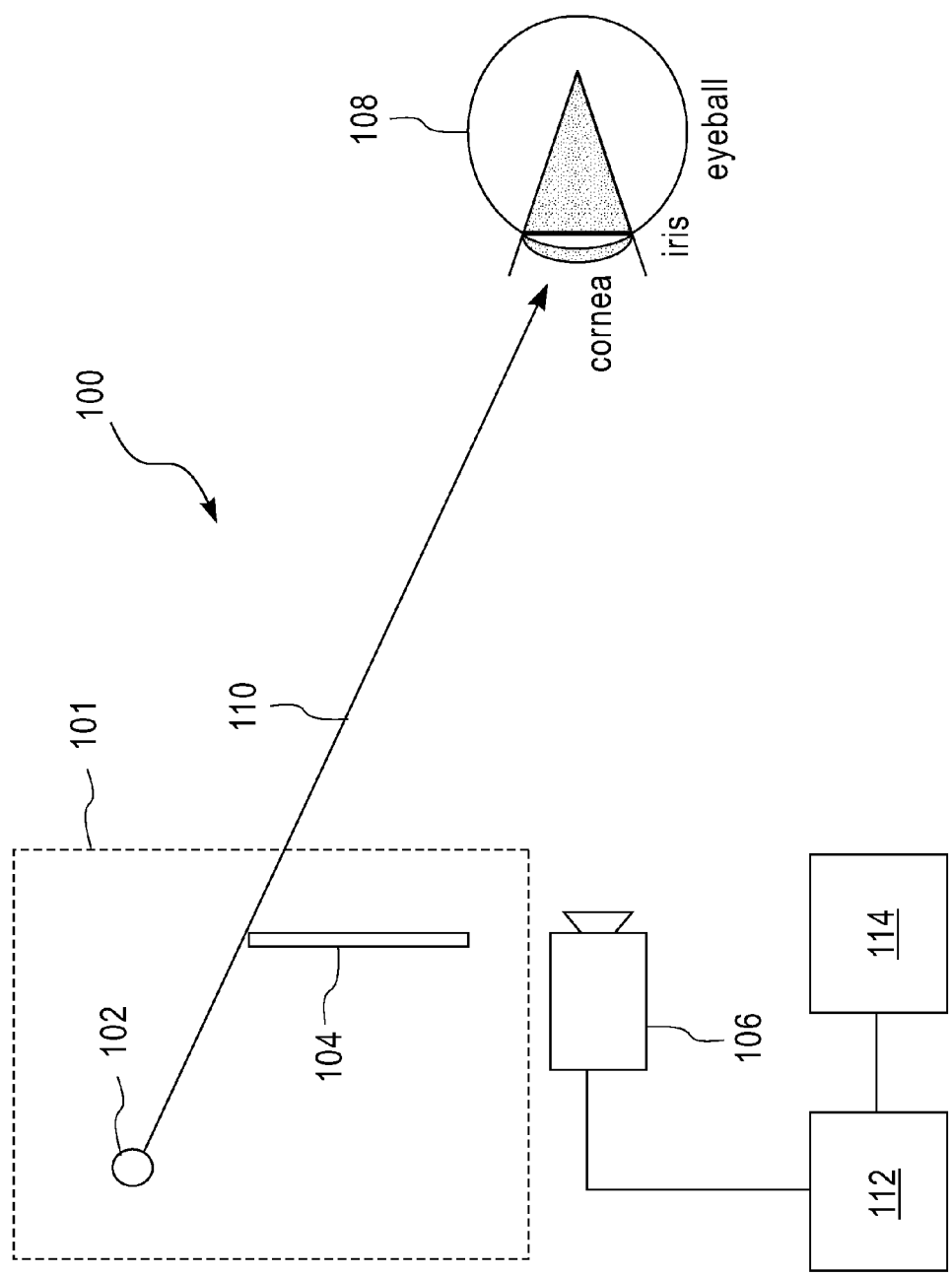
FIG. 1 is an exemplary schematic depicting the system for making biometric measurements or comparisons.

With reference to the FIG. 1, a system 100 for biometric measurement and identification comprises a device for providing a pattern 101. The device for providing a pattern 101 generally comprises source of light 102 and a pattern source 104 (for providing a pattern). The system 100 further comprises an imaging device 106 that is located at a distance $d$, from the source of light 102. The source of light 102 is disposed on a first side of the pattern source 104. The object 108 to be imaged is located on an opposing side (e.g., a second side) of the pattern source 104. The imaging device 106 is in communication with a pattern comparison device 112. While the depiction in the FIG. 1 depicts a source of light 102 and a pattern source 104, projective optics can be used in place of the source of light 102 and the pattern source 104 to dispose an image on the object 108.

The light source 102 can be a source that emits light in the visible, ultraviolet or infrared regions of the electromagnetic spectrum. The light is of an intensity that permits a projection of an image on a diffusely reflecting object and to obtain a reflection from the diffusely reflecting object. Thus a surface that would not reflect an image of, for example, an illuminated computer screen would be capable of reflecting light from the light source 102. It is preferable to use a point source light emitting diode (LED) that emits light in the infrared region of the electromagnetic spectrum.

The pattern source 104 for providing the pattern can comprise an opaque screen or can comprise a screen that has a pattern disposed upon it. The pattern may be a grid that comprises dots, a checkerboard pattern, a cross-hatched pattern, half a plane of light or even a single stripe. In the FIG. 1, the pattern source 104 is an opaque screen. The pattern source 104 is generally disposed between the source of light and the object whose shape is desired. The pattern source 104 is illuminated by the source of light 102. In one embodiment, the light source 102 is a point source light emitting diode (LED), while the pattern source 104 is an opaque screen. The image of the source (either the pattern or the edge of the opaque screen) is then projected onto the object 108. A suitable imaging device 106 such as a camera may be used to capture the image. The imaging device 106 is located at a different location from the source of light 102 and is capable of capturing an image from a diffusely reflecting surface.

The image of the pattern on the object 108 generally reflects the contours of the object 108 being imaged. It is desirable for the object 108 to be capable of reflecting diffuse light. The image of the pattern on the object 108 does not have to be visible to a human. It just has to be perceptible to the imaging device. It is also desirable for the imaging device to be capable of imaging diffusely reflected light (i.e., light reflected from a diffusely reflecting surface). The light source is therefore of an intensity to effectively project an image onto the surface of the object in all conditions.

The pattern comparison device 112 is operative to compare details of the pattern disposed upon the object and details of a reference pattern. The pattern comparison device 112 comprises a database in which reference patterns or characteristics of these patterns for a variety of different objects are stored. The pattern comparison device 112 rejects the object 108 if the pattern disposed upon the object 108 does not match the reference pattern. In one embodiment, the pattern comparison device 112 further comprises a biometric comparison device 114, the biometric comparison device being effective to compare an image of the object to one or more known images to make a biometric identification. If the image of the object does not compare within certain statistical limits to the one or more known images, the pattern comparison device rejects the identification, if the pattern disposed upon the object does not match the reference pattern.

In the FIG. 1, the pattern source 104 is disposed between the source of light 102 and the object 108. The pattern source 104 is an opaque screen. The pattern source 104 is disposed in such a manner that light rays from the light source 102 can illuminate the portion of the object 108 that are above the indicated ray 110. The portion of the object 108 that is below the indicated ray 110 is not illuminated. In other words, an image of the edge of the opaque screen is projected onto the object when the light source is turned on. In one embodiment, the light source 102 and the pattern source 104 for providing the pattern can be merged into a single device. The single device is hereinafter termed a "device for providing a pattern". In other words the light source 102 can provide the pattern that is projected onto the object, when it is turned on.

In one embodiment, in one manner of using the system 100 for making a biometric determination, an object such as an iris is first imaged with the imaging device 106 without turning on the source of light 102. It is then imaged a second time using an illuminated source of light 102. During the imaging of the iris with the illuminated source of light 102, an image of the edge of the pattern source 104 is disposed upon the iris. The profile of this image on the iris is then checked to make sure that the surface is flat. This is because a true iris is actually flat. In one embodiment, the first image (e.g., the uncorrupted image) is used to extract the biometric information while the second image is used to verify the object's geometry.

Figure 2A:
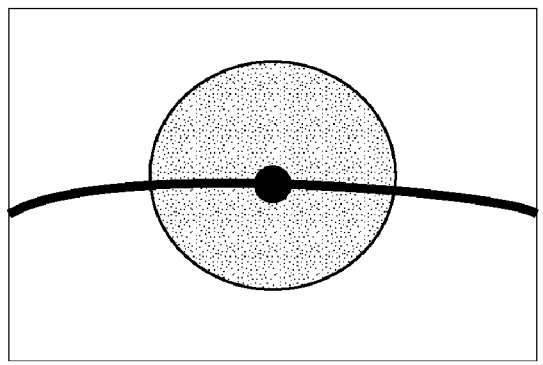
FIG. 2(a) is an exemplary depiction showing the image of the opaque screen on an iris.
Figure 2B:
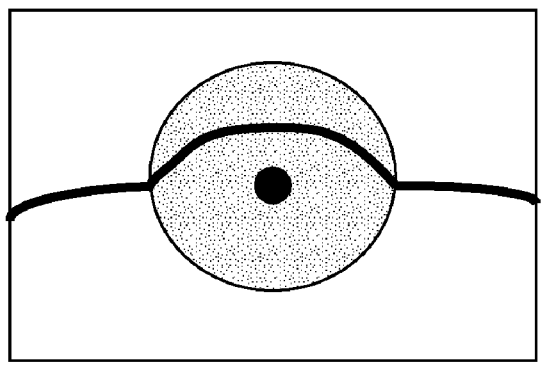
FIG. 2(b) is an exemplary depiction showing the image of the opaque screen on a fake contact lens.

FIGS. 2(*a*) and 2(*b*) are schematic images obtained from a true iris and one that contains a fake contact lens respectively. In the FIGS. 2(*a*) and 2(*b*), the heavy line marks the image of the edge of the opaque screen 104. For the true iris, the line has a flat shape, while for the fake contact lenses the line is curved.

Figure 3B:
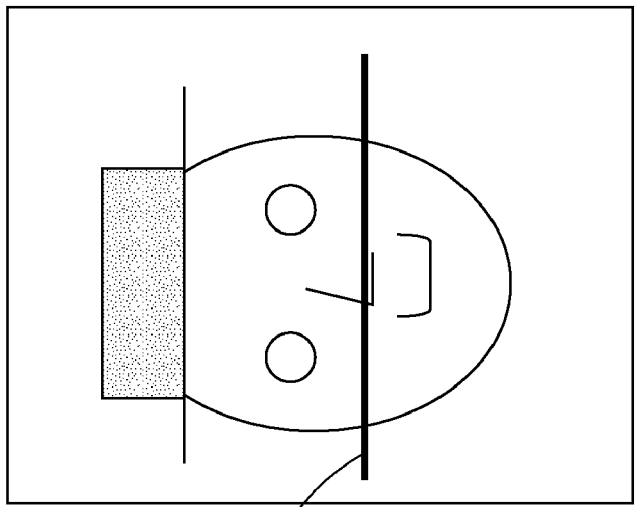
FIG. 3(b) is an exemplary depiction showing the image of the opaque screen on a photograph of the corresponding human face.
Figure 3A:
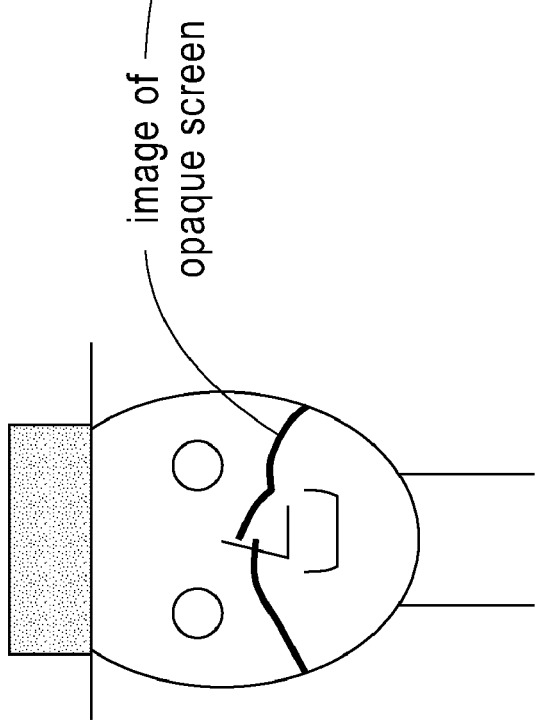
FIG. 3(a) is an exemplary depiction showing the image of the opaque screen on a true human face.

FIGS. 3(*a*) and 3(*b*) depict the image of the edge of the opaque screen when the object 108 is either a human face or a photograph of the human face respectively. FIG. 3(*a*) depicts the shape of the image of the edge (of the opaque screen) on a true human face, while FIG. 3(*b*) depicts the image of the edge when it is disposed upon the photograph of the same human face. For the photograph in the FIG. 3(*b*) (which does not have the contours of an actual human face), the image of the edge of the opaque screen appears as a straight line, while for the actual human face in the FIG. 3(*a*) it appears as a curved line. The appearance of the curved line on the human face is due to the contours of the face. The curved line on the human face reflects the rounding of the nose and the cheeks.

The system disclosed herein can be used to project an image on to any curved surface on the object. Diffuse surfaces that do not reflect light, such as, for example, the human skin or eyelids can be used as a surface on to which an image can be projected. Measurements can be made in the presence of external illumination such as for example in broad daylight, where another source of illumination such as, for example, a computer cannot be used.

The pattern comparison device 112 can contain reference patterns of various objects whose biometric identification is desired. The reference patterns do not necessarily need to be exact replicas of the object whose biometric identification is desired. A generalized specification of the features of the object whose biometric identification is adequate. When a biometric pattern is obtained, it is compared with the reference pattern. If the reference pattern does not match the biometric pattern to within desirable tolerances, the object is rejected.

It is to be noted that while the FIG. 1 depicts a single camera that takes both images—one without the light source being illuminated and another with the light source being illuminated, separate imaging devices may be used to capture the object and the biometric image (e.g., the image of the opaque line). Thus two or more imaging devices may be used to image the object. When a single imaging device (e.g., a camera) is used, then the two images can be taken in quick succession. This prevents substitution of a different source between authentication and signal extraction times.

It is also to be noted that a partial or full 3-dimensional reconstruction of the object is not always desirable. A few statistical measurements of the object can be made and these statistical measurements may be used to make the appropriate comparison of the authenticity of the object.

The aforementioned method and system may be advantageously used for security enhancement without the expense of two cameras. It can also avoid the use of expensive computational techniques.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention.

What is claimed is:

1. A biometric system comprising:
 a device for providing a pattern; the device comprising:
  a source of light; the source of light being of an intensity that is effective to project a pattern onto a diffusely reflecting object; and
  a source for providing the pattern; the source for providing the pattern being disposed between the source of light and the diffusely reflecting object upon which an image of the pattern is disposed; the source for providing the pattern being illuminated by the source of light; the pattern being disposed upon the object;
 an imaging device; the imaging device being disposed at a different location from the source of light; the imaging device being operative to obtain an image from light that is diffusely reflected from the object;

a pattern comparison device; the pattern comparison device being operative to compare details of the pattern disposed upon the object and details of a reference pattern; and a biometric comparison device; the biometric comparison device being effective to compare an image of the object to one or more known images to make a biometric identification; the pattern comparison device rejecting the identification, if the pattern disposed upon the object does not match the reference pattern.

2. The biometric system of claim 1, wherein the imaging device is a camera.

3. The biometric system of claim 1, wherein the source for providing a pattern is an opaque screen.

4. The biometric system of claim 1, wherein the pattern is a grid, a checkerboard pattern, a cross-hatched pattern, half a plane of light or a single stripe.

5. The biometric system of claim 1, wherein the source of light is a point source light emitting infrared diode.

6. The biometric system of claim 1, wherein the object is one of a human face or a human iris.

* * * * *